US00PP37175P2

(12) United States Plant Patent
Horvath

(10) Patent No.: US PP37,175 P2
(45) Date of Patent: Dec. 23, 2025

(54) ***PYCNANTHEMUM INCANUM* PLANT NAMED 'Smokey Mountain Mint'**

(50) Latin Name: *Pycnanthemum incanum*
Varietal Denomination: Smokey Mountain Mint

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 18/831,389

(22) Filed: Dec. 30, 2024

(51) Int. Cl.
*A01H 5/02* (2018.01)
*A01H 6/50* (2018.01)

(52) U.S. Cl.
USPC ..... Plt./263.1
CPC ..... *A01H 6/50* (2018.05)

(58) Field of Classification Search
USPC ..... Plt./263.1
CPC ..... A01H 5/02
See application file for complete search history.

*Primary Examiner* — Kent L Bell

(57) ABSTRACT

A new, distinct *Pycnanthemum* hybrid plant, named 'Smokey Mountain Mint', as illustrated and described, characterized by the darker colored foliage of its new and mature growth.

2 Drawing Sheets

Figure 1:
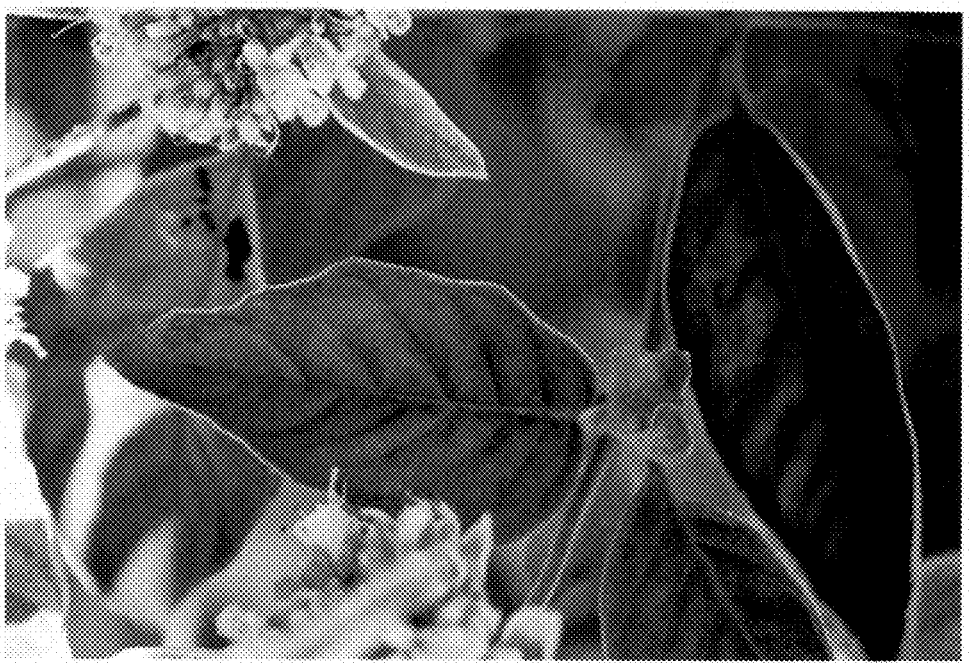

Latin name: *Pycnanthemum incanum.*
Cultivar name: 'Smokey Mountain Mint'.

BACKGROUND OF THE INVENTION

The present invention relates to a new and distinct cultivar of *Pycnanthemum incanum* plant, botanically known as *Pycnanthemum incanum* and hereinafter referred to by the name 'Smokey Mountain Mint'. The new *Pycnanthemum incanum* plant is a product of a planned breeding program conducted by the inventor in Hebron, IL, USA. The objective of the breeding program is to create vigorous new *Pycnanthemum* plants that are more colorful in foliage and flower. This *Pycnanthemum* was selected for the darker colored foliage of its new and mature growth. The new *Pycnanthemum incanum* plant was discovered and selected by the inventor as a single flowering plant from within the progeny of the stated cross-pollination of an unnamed plant of *Pycnanthemum incanum* as the female parent and an unnamed plant of *Pycnanthemum incanum* as the male parent, grown in a controlled environment in Hebron, IL, USA during the summer of 2022. Asexual reproduction of the new *Pycnanthemum incanum* plant by softwood cuttings in Hebron, IL, USA since the winter of 2023, have shown that the unique features of this new *Pycnanthemum incanum* plant are stable and reproduced true to type in successive generations. No plants of the new *Pycnanthemum incanum* have been sold in this country, or anywhere in the world, prior to the filing of this application, nor has any disclosure of the new plant been made prior to the filing of this application with the exception of that which was disclosed by the inventor and his company, Intrinsic Perennial Gardens, Inc within one year of filing of this application and was derived directly from the inventor.

SUMMARY OF THE INVENTION

Plants of the new *Pycnanthemum incanum* have not been observed under all possible environmental conditions and cultural practices. The phenotype may vary somewhat with variations in environment such as temperature and light intensity without, however, any variance in genotype.

The following traits have been repeatedly observed and are determined to be the unique characteristics of 'Smokey Mountain Mint'.

These characteristics in combination distinguish 'Smokey Mountain Mint' as a new and distinct *Pycnanthemum incanum* plant:

1. New developing foliage, colored: 191 A at the upper surface, 191 A at the mid section of the stem and 194 B at the base of the stem.
2. Mature foliage, both upper and lower surface colored: N187 B and N187 B.
3. Silvered bracts, colored 191 A on top of the stems near the flowers.

Plants of the new *Pycnanthemum incanum* differ primarily from the male and female parent, an unnamed *Pycnanthemum incanum* plant in the following characteristics:

1. Leaves of plants of the new *Pycnanthemum incanum* are darker in color than leaves of the male and female parent.
2. Plants of the new *Pycnanthemum incanum* are 65 cm tall while plants of from the male and female parent are 75 cm or taller.

Plants of the new *Pycanthemum incanum* differ primarily *Pycnanthemum muticum*, an unnamed seedling. in the following characteristics:

1. Leaves of plants of the new *Pycnanthemum incanum* are darker in color than leaves of *Pycnanthemum muticum*, an unnamed seedling.
2. Plants of the new *Pycnanthemum incanum* are 65 cm tall while plants of *Pycnanthemum muticum*, an unnamed seedling are 75 cm or taller.

There are no known cultivars of *Pycnanthemum incanum* or *Pucnanthemum muticum* that the inventor is aware of to compare to.

DESCRIPTION OF PHOTOGRAPHS

The accompanying colored photographs illustrate the overall appearance of the new *Pycanthemum* hybrid plant showing the colors as true as it is reasonably possible to obtain in colored reproductions of this type. Colors in the photographs may differ slightly from the color values cited in the detailed botanical description which accurately describe the actual colors of the new *Pycnanthemum incanum* plant.

FIG. 1. Close up of the new foliage on a one-year old plant in Hebron, IL USA.

Figure 2:
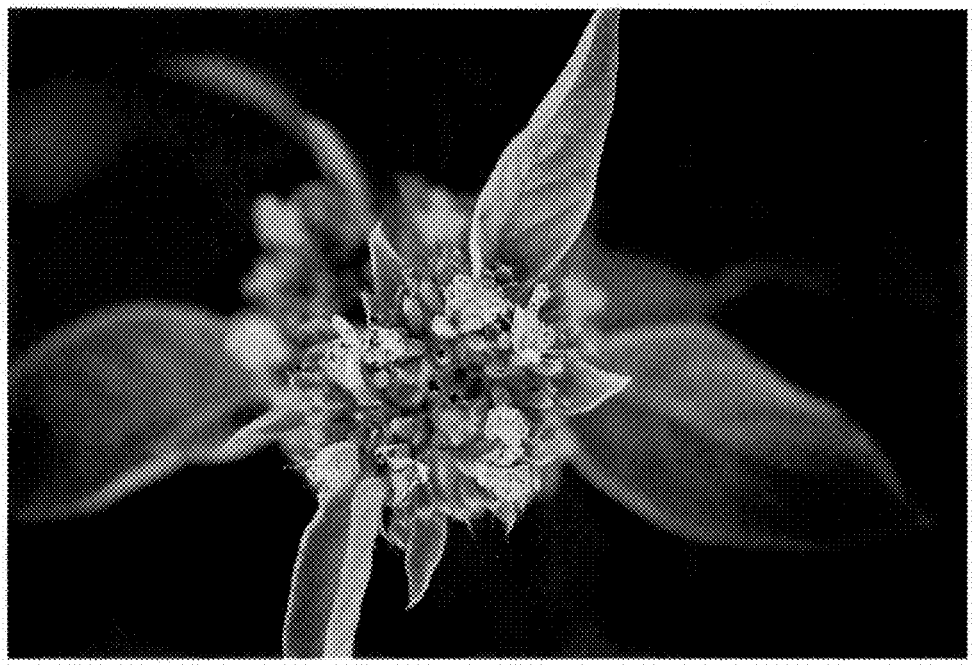

FIG. 2. Close up flower in June on a one-year old plant in Hebron, IL USA.

Figure 3:
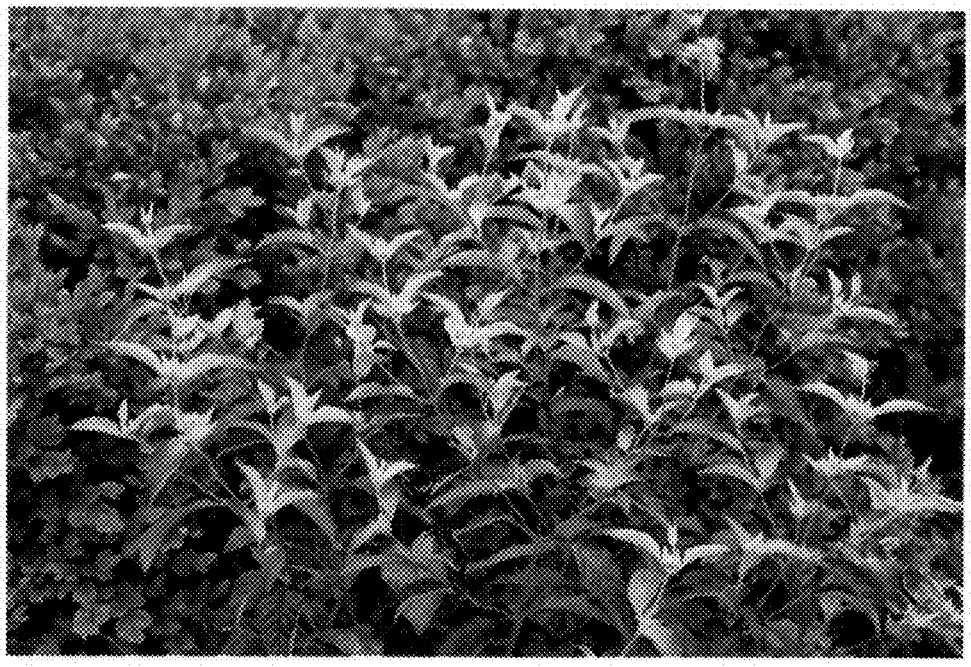

FIG. 3. Foliage and flowers on a one-year old plant in Hebron, IL USA.

Figure 4:
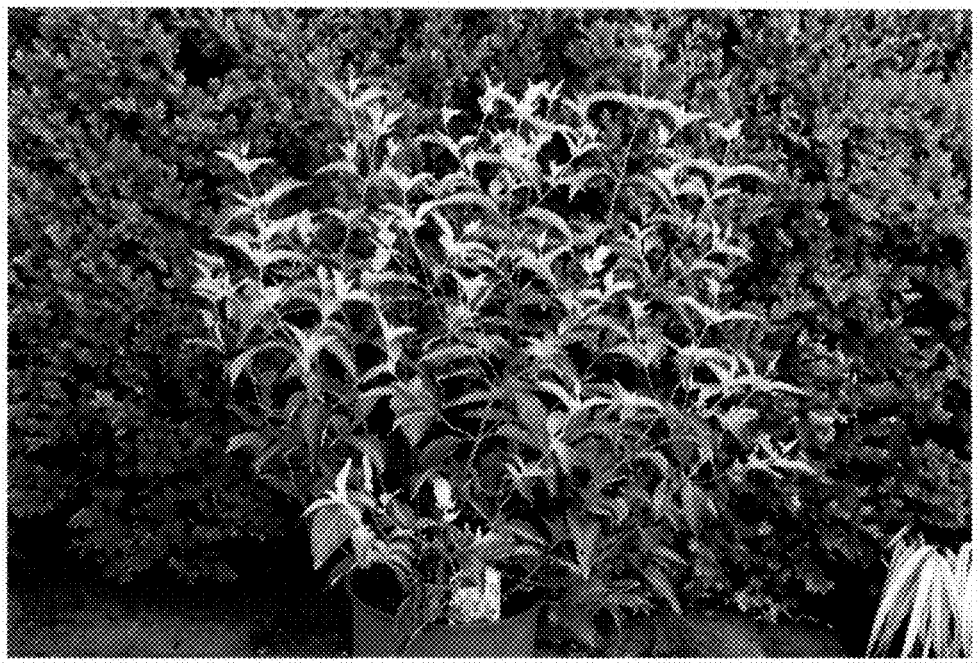

FIG. 4. Overall plant habit on a one-year old plant in Hebron, IL USA.

DETAILED BOTANICAL DESCRIPTION

The aforementioned photographs and following observations, measurements and values describe one-year old plants grown during the summer in an outdoor nursery in Hebron, IL USA and under typical production conditions. In the detailed description, color references are made to The Royal Horticultural Society Colour Chart, 2001 Edition, except where general terms of ordinary dictionary significance are used.

Plant description:

*Botanical classification.*—*Pycnanthemum incanum.*

Parentage:

*Female, or seed, parent.*—*Pycnanthemum incanum*, unnamed seedling.

*Male, or pollen, parent.*—*Pycanthemum incanum*, unnamed seedling.

Propagation:

*Type cutting.*—By softwood cuttings.

*Time to initiate roots, summer.*—About two weeks.

*Time to produce a rooted young plant, summer.*—About two months.

*Root description.*—Fine, fibrous; 199 C in color.

*Rooting habit.*—Freely branching; dense.

Plant description:

*Plant and growth habit.*—Perennial, upright and outwardly spreading plant form; broad; basal branching habit; vigorous growth habit.

Plant height.—65 cm.

Plant width.—750 cm.

*Lateral branch description.*—Length: About 27 cm. Diameter: About 2-3 mm.

Internode length: About 6-8 cm. Strength: Strong. Aspect: Upright. Texture: Glabrous. Color: 187 B near the top of the plant to as dark as N186 A at the base. Number of lateral branches — 30.

Foliage description:

*Arrangement.*—Opposite, simple. Length. — About 9 cm. Width. — About 35 mm.

*Shape.*—Ovate. Apex. — Acute. Base. — Oblique. Margin. — Serrate.

*Texture, upper and lower surfaces.*—Glabrous.

*Venation pattern.*—Pinnate. Venation color. — Upper surface — N186 B, lower surface N186 B.

*Color.*—Newly developing leaves, Upper surface: 191 A at the tips and 194 B at the base, lower surface 194 B. Mid-section of the newly developing leaves. Upper surface: 191A at the tips and 194 B at the base, lower surface 194 B. Developing leaves, upper surface: 146 A lower surface: 148 C. Mature leaves, upper surface: N186 B, lower surface N187 B and N187 C.

*Petiole size.*—Length. — About 7 mm and diameter. — About 1 mm.

*Petiole color, upper and lower surface.*—187 B and 187 C.

*Texture, upper and lower surfaces.*—Glabrous.

Flower description:

*Flower form, arrangement and flowering habit.*—Single labiate and sessile flowers arranged in terminal globular cluster; flowers face outwardly; freely flowering habit with about 150 flowers developing per inflorescence and around 6000 per plant.

*Natural flowering season.*—Continuous flowering from early July into August in Hebron, IL, USA.

*Flower longevity on the plant.*—About five days; flowers not persistent.

*Fragrance.*—Faintly fragrant; minty, pleasant.

*Flower buds.*—Length: About 4 mm. Diameter: About 1 mm. Shape: Narrowly oblanceolate. Color: N155 C.

*Inflorescence size.*—Length: About 20 mm. Diameter: About 25 mm.

*Inflorescence bracts, typical and observed.*—Arrangement: subtending, Number: 5, Shape: ovate, Length: about 20 mm. Width: 5 mm. Apex: acute, Margin: entire, Bract color: 191 A, Base: truncate, Color upper and lower surface: 191 A At the base.

*Flowers.*—Diameter: About 5 mm. Depth: About 5 mm.

*Petals.*—Arrangement: Labiate; upper lip hooded; lower lip, a single lobe; lips fused. Length, upper and lower lips: About 5 mm. Width, upper lip: About 5 mm. Width, lower lip: About 5 mm. Shape, upper lip: Lanceolate; apex, narrowly acute. Shape, lower lip: Oblanceolate; apex, aristate. Margin, upper and lower lips: Entire. Texture on both the upper and lower lip, upper and lower surfaces: Glabrous. Color: When opening, upper and lower surfaces of upper lip: 83 B becoming 83 B, When opening, spotted lower lip: 83 B and when fully opened, upper and lower surfaces upper lips have color: N155 D close to near white, lower lip: close to N155 D. Background color of the lip is N155 D when opening and mature, purple spots are 83 B when opening and mature.

*Sepals.*—Arrangement: Five in a single whorl: fused, tubular. Length: About 5 mm. Width: About 1 mm. Apex: Narrowly acute. Margin: Entire. Texture, upper and lower surfaces: glabrous. Color: When opening, upper and lower surfaces and fully opened, upper and lower surfaces: N155 D with purple spots of 83 A and 83 B.

*Reproductive organs.*—Stamens: Quantity per flower. Two. Filament length. About 3 cm. Filament color: Close to N155 B. Anther length: About 5 mm. Anther shape: Narrowly elliptic. Anther color: Close to 185 B. Pollen amount: Scarce. Pollen color: close to N155 D. Pistils: Quantity per flower: One. Pistil length: About 8 mm. Stigma shape: Cleft. Stigma color: N155 D. Style length: 1 cm. Style color N155 D. Ovary color 197 A.

*Seed and fruit.*—Seed and fruit production have not been observed.

Disease resistance: Plants of the new *Pycanthemum incanum* have not been observed to be resistant to common diseases to other *Pycnanthemum* plants and species.

Pest resistance: Plants of the new *Pycanthemum incanum* have not been observed to be resistant to pests common to *Pycnanthemum* plants.

Garden performance: Plants of the new *Pycnanthemum incanum* have exhibited good tolerance to rain and wind, have been observed to be hardy to USDA Zone 5 and to tolerate high temperatures of about 35° C.

I claim:

1. A new and distinct *Pycnanthemum incanum* plant named 'Smokey Mountain Mint', as illustrated and described herein.

* * * * *